(12) United States Patent
Erbel

(10) Patent No.: US 6,898,456 B2
(45) Date of Patent: *May 24, 2005

(54) METHOD FOR DETERMINING A CURRENT LUNG FILLING EXTENT AND METHOD FOR ASSISTING RADIATION THERAPY DURING RESPIRATORY SHIFTING OF THE RADIATION TARGET

(75) Inventor: Stephan Erbel, München (DE)

(73) Assignee: BrainLAB AG, Kirchheim/Heimstetten (DE)

( * ) Notice: Subject to any disclaimer, the term of this patent is extended or adjusted under 35 U.S.C. 154(b) by 279 days.

This patent is subject to a terminal disclaimer.

(21) Appl. No.: 09/860,036

(22) Filed: May 17, 2001

(65) Prior Publication Data

US 2002/0115923 A1 Aug. 22, 2002

(30) Foreign Application Priority Data

Nov. 22, 2000 (EP) .......................................... 00125227

(51) Int. Cl.$^7$ ................................................ A61B 5/00
(52) U.S. Cl. ...................... 600/428; 600/407; 600/413; 600/427; 600/437; 606/103; 128/899
(58) Field of Search ............................... 600/407–482; 606/130; 128/899

(56) References Cited

U.S. PATENT DOCUMENTS

| 5,287,276 A | 2/1994 | Crawford et al. |
| 5,538,494 A | 7/1996 | Matsuda |
| 5,588,439 A | 12/1996 | Hollub |
| 5,859,891 A * | 1/1999 | Hibbard ........................ 378/62 |
| 6,076,005 A * | 6/2000 | Sontag et al. ................ 600/413 |
| 6,175,761 B1 * | 1/2001 | Frandsen et al. ............ 600/436 |
| 6,731,970 B2 * | 5/2004 | Schlossbauer et al. ...... 600/428 |

FOREIGN PATENT DOCUMENTS

DE   198 29 224 A   1/2000

OTHER PUBLICATIONS

Kubo H D et al: "Respiration Gated Radiotherapy Treatment: A Technical Study" Physics in Medicine and Biology, GB, Taylor and Francis Ltd. London. 1996.

* cited by examiner

Primary Examiner—Max F. Hindenburg
Assistant Examiner—William C. Jung
(74) Attorney, Agent, or Firm—Renner, Otto, Boisselle & Sklar, LLP

(57) ABSTRACT

The invention concerns a method for determining the filling of a lung, wherein the movement of an anatomical structure which moves with breathing, or one or more points on the moving anatomical structure whose movement trajectory is highly correlated with lung filling, is detected with respect to the location of at least one anatomical structure which is not spatially affected by breathing, and wherein each distance between the structures is assigned a particular lung filling value. It further concerns a method for assisting in radiotherapy during movement of the radiation target due to breathing, wherein the association of lung filling values with the distance of the moving structure which is identifiable in an x-ray image and the structure which is not spatially affected by breathing is determined by means of an above-named method, the current position of the radiation target is detected on the basis of the lung filling value, and wherein radiation exposure is carried out, assisted by the known current position of the radiation target.

18 Claims, 7 Drawing Sheets

METHOD FOR DETERMINING A CURRENT LUNG FILLING EXTENT AND METHOD FOR ASSISTING RADIATION THERAPY DURING RESPIRATORY SHIFTING OF THE RADIATION TARGET

BACKGROUND OF THE INVENTION

Technical Field

The invention concerns a method for determining the current filling of a lung in accordance with claim 1, and a method for assisting in radiotherapy during movement of the radiation target due to breathing in accordance with claim 8.

Irradiating tumours in the area of the lung, liver and kidneys is made significantly more difficult by the fact that these areas experience movement due to breathing. Only insufficient systems currently exist for detecting and/or measuring this movement. In present clinical practice, patients are "mapped" in CT or in a transillumination image, i.e. a planning data set is produced, and a target volume marked in and localised within a patient co-ordinate system (for example, using markings on the skin). The problem with this, however, is that the position of said target volumes is affected by the amount of air which the patient has in his lungs while the CT is being taken. The position of the target volume established during planning is therefore only valid for precisely one lung filling. FIG. 1 illustrates the movement of the target volume according to variations in lung filling when the patient is breathing freely.

The patient's lung filling is the quantity which affects the position of the target volume within the patient's body. Tracking the patient's lung filling over time establishes that it changes with each breath (this is the approximately 0.5 liters of air which the patient breathes in and out). Tracking the lung filling over a longer period of time, however, establishes that the breath maximum, minimum and median likewise change over time, as illustrated in FIG. 2, which shows lung filling variation over time.

It cannot therefore be predicted for any selected point in time (or short period of time) in the future, where the maximum, minimum and median of a patient's lung filling will be situated. The problem exists that a 3D planning data set cannot be transferred to the state of the patient at the time of radiation exposure. If the planning data set has been taken with the patient holding his breath (this normally being the planning CT), this data set represents the patient and the target volume at a particular lung filling. In order to be able to transfer these data to the state of the patient at the time of radiation exposure, the lung fillings at the two points in time would have to correspond precisely. If the patient is able to breathe freely during radiation exposure, this is the case at most twice in each breath. Since patients—who have to hold their breath for about 10 to 20 seconds for the planning CT—have a tendency just before it to breathe in or out more strongly or more weakly than in normal breathing, it can also occur that during radiation exposure the patient at no point has the same lung filling as in the reference (planning) data set. In this case, the position of the target volume is at no point known, and pin-point irradiating is thus impossible.

In many medical practices, it would therefore be advantageous to be able to detect the patient's breathing precisely, in order for example to be able to track the position of organs or tumours affected by breathing. For this purpose, methods have already been developed for detecting changes in external parameters of the patient, so allowing the patient's breathing to be detected. The patient's breathing can also be tracked by spirometry. The problem with these solutions, however, is that breathing can only be tracked as long as the patient remains in contact with the system. If, however, it is necessary to compare the patient's breathing at two, somewhat far apart, points in time, the above-named systems would have to be permanently in contact with the patient. Since in many medical practices this is impossible or undesirable, such uninterrupted contact is not, as a rule, available. In all hitherto known methods, the problem arises that it is not possible to find a zero point or another absolute reference point again with satisfactory precision. Where measuring has been interrupted between the acquisition of readings, these readings cannot then be directly compared. The unsatisfactory precision is caused for instance by sebaceous layers, and the reference markings arranged on them, slipping, or in spirometry by the inability to reproduce the maximum and minimum lung filling.

SUMMARY OF THE INVENTION

It is the object of the present invention to provide a method for determining the current filling of a lung and a method for assisting in radiotherapy during movement of the radiation target due to breathing, which solve the problems outlined above. In particular, the irradiation of radiation targets which move due to breathing is to be optimised.

This object is solved in accordance with the invention, firstly by a method for determining the filling of a lung, wherein the movement of an anatomical structure which moves during breathing, or one or more points on the moving anatomical structure whose movement trajectory is highly correlated with lung filling, is detected with respect to the location of at least one anatomical structure which is not spatially affected by breathing, and wherein each distance between the structures is assigned a particular lung filling value.

The invention thus solves the above-named problems by using a parameter which is not distorted by external references slipping, which describes the patient's breathing unambiguously, and which may be detected by measurement at reasonable expense. The distance described above provides such a parameter, from which it is possible to track breathing precisely, at any point in time, i.e. to positively determine lung filling at any time, even when detected at different times. On the basis of this knowledge, any further detecting and treatment may be performed all the more precisely, and optimally.

In an embodiment of the invention, detection is performed by producing transillumination images, in particular x-ray images, wherein preferably at least two images are produced and the remaining lung filling values are interpolated.

Furthermore, detection may be performed by producing images from tomographic imaging methods, for example CT, MR, or PET methods, wherein preferably at least two images are produced and the remaining lung filling values are interpolated. Digitally reconstructed x-ray images are advantageously used here as the images, obtained from a data set of a tomographic imaging method.

Particularly advantageous is the use of parameters which in addition to the three requirements above (no slipping, unambiguous description of the patient's breathing and measurement at reasonable expense) may be detected both by transillumination as well as in three-dimensional planning data sets. In accordance with the invention, the anatomical structure which moves during breathing is therefore advantageously a structure which is identifiable in a transillumination, in particular in an x-ray image, preferably the pulmonary diaphragm or a point on the pulmonary diaphragm.

Thus, a characteristic point of a structure of the human anatomy is considered, which is moved by breathing and is visible both in x-ray images and in three-dimensional planning data sets, for example the pulmonary diaphragm. If the distance between this reference and the anatomical structure which is not spatially affected by breathing (and therefore not moved by breathing), for example a vertebral body or part of a vertebral body, in particular the edge of a vertebral body, is determined and tracked, a value is obtained which is very highly correlated with the patient's lung filling.

Alternatively, it is equally possible to measure the apparent distance between the two references in a two-dimensional image. However, in order that readings from various two-dimensional representations may be directly compared, it is necessary for the projection parameters of the two representations to be identical (angle of view and distance corresponding to one another in digitally reconstructed x-ray images, and genuine x-ray images). Accordingly, the invention also contemplates detecting first by producing transillumination images, in particular x-ray images, and second by producing corresponding images from tomographic imaging methods, for example CT, MR, or PET methods, wherein preferably at least two images are always produced and the remaining lung filling values are interpolated, and wherein a comparison and alignment of the particular lung filling values results.

A further aspect of the invention concerns a method for assisting in radiotherapy during movement of the radiation target due to breathing, wherein:

the association of lung filling values with the distance between the moving structure which is identifiable in an x-ray image and the structure which is not spatially affected by breathing is determined;

the current position of the radiation target is detected on the basis of the lung filling value; and wherein:

radiation exposure is carried out, assisted by the known current position of the radiation target.

In other words, this method includes establishing both the lung filling which the patient had while one or more planning data sets were recorded, as well as the lung filling which the patient had during radiotherapy. By combining the corresponding information, the position or movement of the radiation target may also be determined, by means of the data from the planning data set (these data include the position of the radiation target) and the data from the current transillumination (these data do not, for the most part, include the position of the radiation target, in particular in the case of x-ray images, in which for example a tumour often cannot be made sufficiently visible, but do include the current position of position-trackable tracking devices, for example markings), using the known lung filling as a link. For both data sets include the distance between the moving and stationary structures, from which the lung filling may be deduced. The position of the target volume is, in particular, determined for a number of lung fillings, such that the position of the target volume may then be calculated from the lung filling.

In an embodiment variant, the current position of the target volume is detected on the basis of the lung filling value, by:

detecting the positional course of a radiation target while detecting the movement of the moving structure, and assigning each distance value, i.e. each lung filling value, a positional value of the radiation target;

taking at least one, preferably at least two, transilluminations before radiation exposure, in which the movement of the moving anatomical structure with respect to the position of a locational tracking device, in particular a marking on the patient, is detected, and assigning each distance between the structure and the markings a particular lung filling value;

determining a dependence of the current position of the radiation target upon the positional information from the tracking device, in particular the position of the marking, from the associations of the position of the radiation target with the lung filling value, and the lung filling value with the positional information from the tracking device, in particular the position of the marking.

The association of lung filling values with the distance between the moving structure and the structure which is not spatially affected by breathing may be determined by means of x-ray images digitally reconstructed from a tomographic imaging data set (DDRs), corresponding in angular position and recording distance to the transilluminations before or during radiation exposure.

The current position of the radiation target may be detected on the basis of the lung filling value in real time, or deferred.

The positional information from the tracking device may be obtained by evaluating the data of at least one of the following devices and/or methods, which provide parameters affected by breathing:

markings, in particular arrangements of reflecting markers, preferably for infrared light, which may be positionally detected and tracked in space by means of a computer-assisted tracking system;

monitoring the contours of the patient using video cameras, for instance with an interference pattern or by means of polarised light;

wire strain gauges;

spirometry;

electromyography;

mechanically scanning one or more points on the surface of the patient, in particular by means of a co-ordinate measuring machine.

Knowledge of the current position of the radiation target may be used to control the switching on and off of the therapy beam, and in particular used for only switching the therapy beam on when the radiation target is within a selectable range of tolerance about the radiation target or the axis of radiation of a therapy device. Furthermore, or in addition, this knowledge of the current position of the radiation target, and therefore of the points nearest the head and nearest the feet, may be used to position one of the end points of its movement trajectory, relative to the target point or the target axis of a therapy device, in such a way that an optimally high proportional radiation exposure time is achieved in breath-controlled radiation exposure. After breathing out, the radiation target or target volume remains motionless for almost a second. For this reason, it is particularly useful to irradiate the target volume at this time, since an acceptable proportional radiation exposure time is obtained, with minimal residual movement of the target volume.

Moreover, it is possible to use the knowledge of the current position of the radiation target to carry out dynamic repositioning during radiation exposure, to take into account medium-term variations in the boundary values, namely the minimum and maximum, of the patient's lung filling. If, for instance, during breathing the patient has increasingly less air in his lung, the mean position of the target volume in the patient shifts; the two extrema of the current movement trajectory likewise shift. This can lead to the target volume no longer traversing the target point/target axis of the radiotherapy apparatus, or the target volume traversing the target point/target axis of the radiotherapy apparatus too fast. This may be compensated for by correspondingly shifting the patient relative to the radiotherapy apparatus.

Movement of the radiation target within the patient may be compensated for by a continuous, reverse movement of the patient on a patient's table. Furthermore, artificially forced breathing may be used to induce a state in the patient in which the lung filling value corresponds to the value determined from the association of lung filling values with the distance between the moving structure and the structure which is not spatially affected by breathing, therefore in particular in the planning stage, using the tomographic images.

BRIEF DESCRIPTION OF THE DRAWINGS

An embodiment of the invention will now be explained. The drawings show.

DETAILED DESCRIPTION

The embodiment of the invention will now be explained by means of a chronological illustration of the procedure.

Firstly, the planning data sets are recorded. In contrast to the conventional procedure, the patient is not scanned only once, but at least twice. Any tomographic imaging methods are possible here as the image-generating method (MR, CT, PET . . . ). It is necessary here that the images are produced while the patient holds his breath, and that the lung filling is different in the different images (preferably, one scan after breathing in, one scan after breathing out). The target area is defined in both data sets in the conventional way.

At each stage of radiation exposure, one or more markers are stuck to the patient's thorax which move with the patient's breathing. The position of these markers is tracked in real time via a computer- and camera-assisted tracking system. At least two x-rays images are taken of the patient, distributed over a breathing cycle (for example, using x-ray sources on the ceiling; the image is recorded by a digital detector under the patient). The angle of view from which the x-ray images are recorded has to be known; the position of the markers on the patient's thorax at the time the images are recorded is stored.

Figure 1:
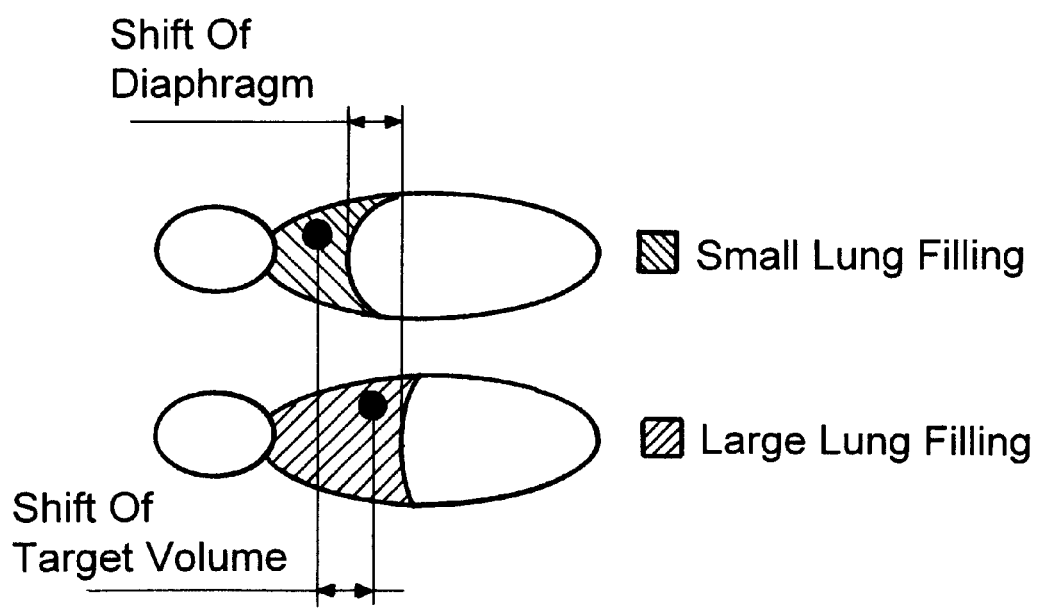
FIG. 1 the target volume moving with variations in the lung filling of the freely breathing patient.
Figure 2:
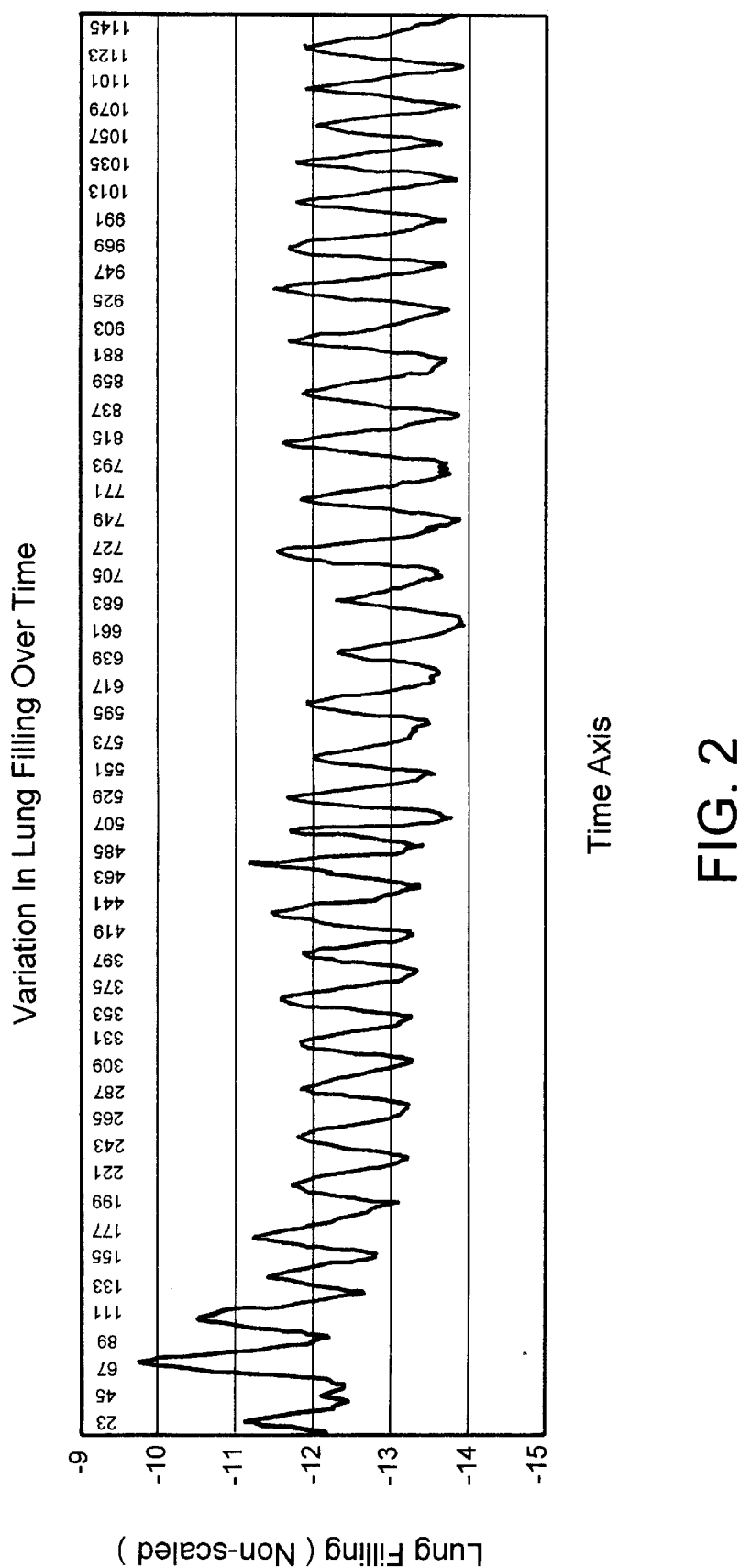
FIG. 2 variation in the lung filling over time.
Figure 3:
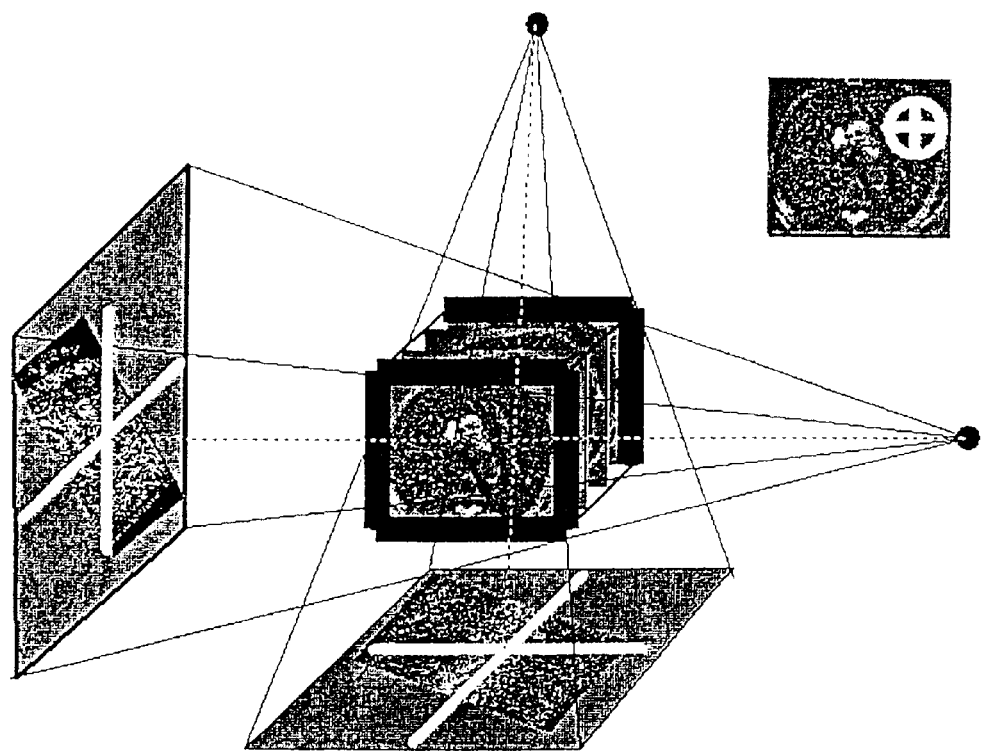
FIG. 3 a schematic representation of how a digitally reconstructed x-ray image (DDR) is calculated.
Figure 4:
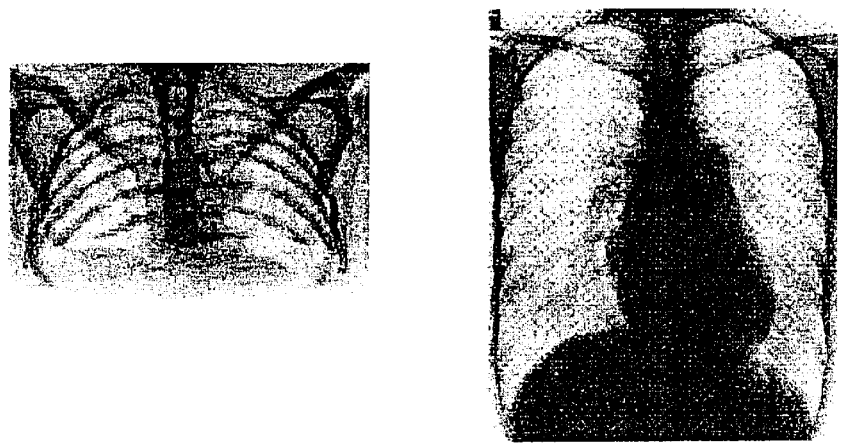
FIG. 4 a comparison between a DDR and a corresponding x-ray image.

Through corresponding geometric calculations, a "digitally reconstructed x-ray image" (DDR) matching the angle of view from which the x-ray images were taken may be calculated from each of the 3D planning data sets. FIG. 3 schematically shows how such an image, which also contains positional information regarding the radiation target, is calculated. A comparison between a DDR (left) and a corresponding x-ray image of the thorax may be seen in FIG. 4.

The image range of the x-ray images and the DDRs is selected such that the pulmonary diaphragm is identifiable on the image. (The pulmonary diaphragm is, so to speak, the border between the lung and the liver lying beneath it). Due to the high distance in density, this separating line is identifiable both in the DDRs and in the x-ray images. The position of the pulmonary diaphragm in the patient's thorax defines the patient's lung filling at any given point in time.

Figure 5:
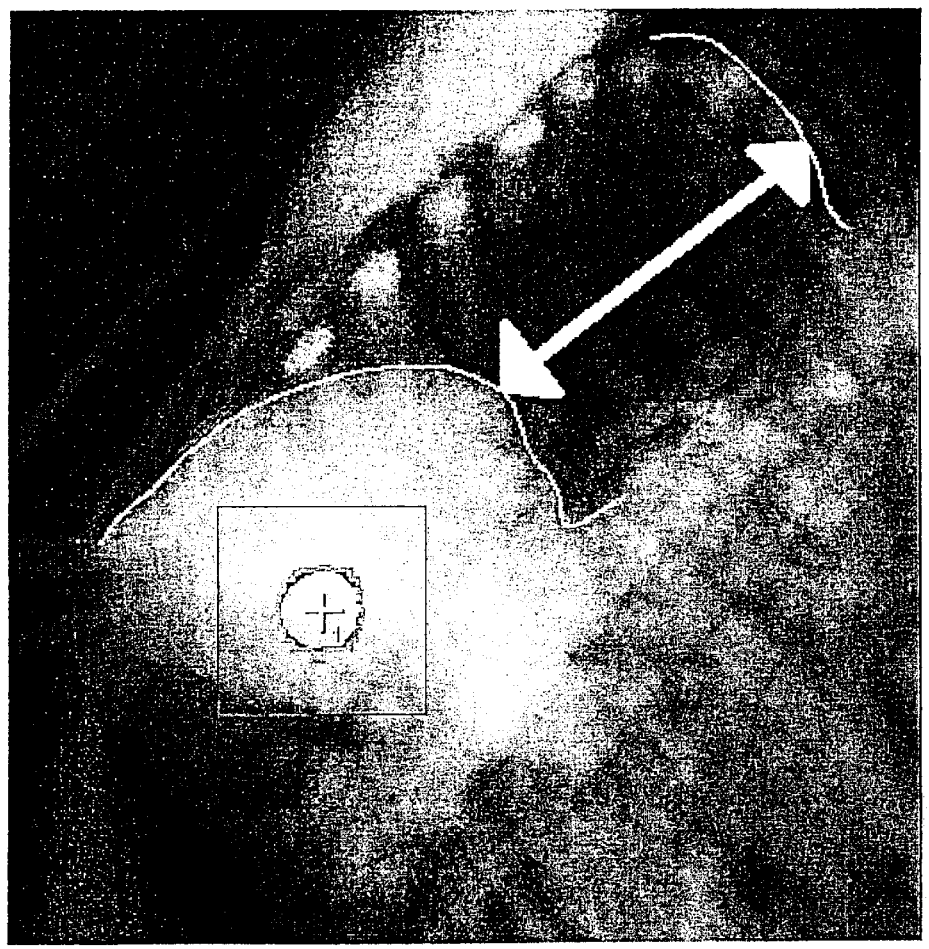
FIG. 5 a transillumination image in which the radiation target and the distance between the pulmonary diaphragm and a characteristic point on the skeleton which is not spatially affected by breathing are indicated.
Figure 6:
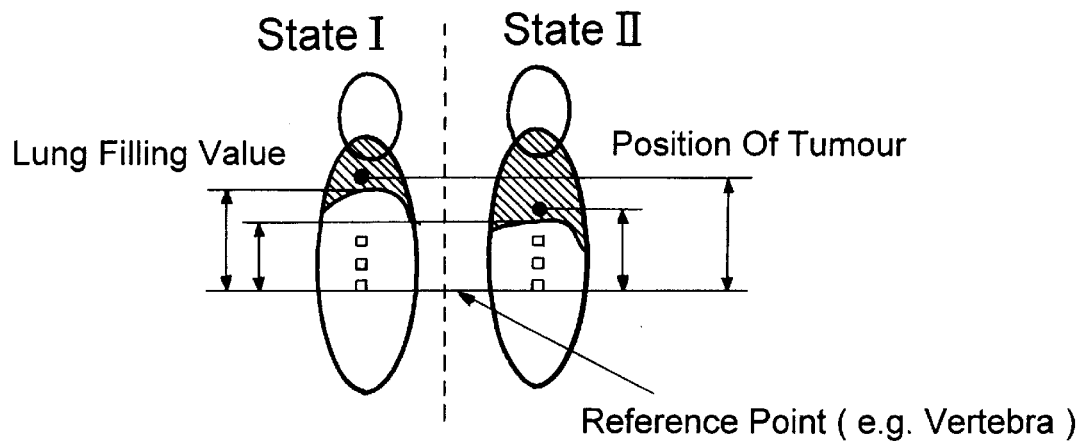
FIG. 6 the lung filling and the position of a tumour in two different breathing states.

Accordingly, the diaphragm may be marked in, by hand or automatically, in the given images, as shown in an example in FIG. 5. If the distance between a characteristic point which does not move with breathing (this can be, for example, a contour of a vertebral body, or a rib) and a point on the diaphragm is measured in each image, then the corresponding image may be assigned a value which unambiguously describes the patient's lung filling. The value measured in this way shall be indicated in the following as the "lung filling value". FIG. 6 schematically shows the distance between the diaphragm and a characteristic point on the skeleton in two different breathing states (states I and II).

The data generated in this way are then paired up in relation to one another, and a relationship is obtained between the position of the tumour and the lung filling value (the position of the diaphragm). One should note here that the representations, simplified for better comprehension, only show the procedure in one spatial co-ordinate (the head-foot direction). The position of the tumour, however, has to be determined in all three spatial co-ordinates, and the correlations determined for all axes.

Figure 8:
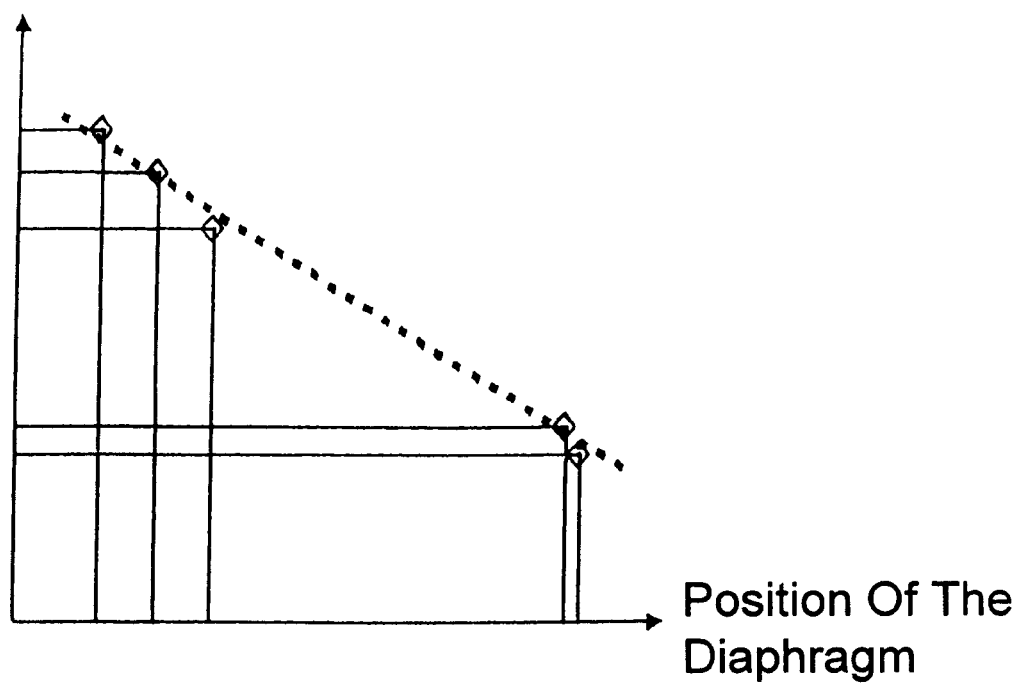
FIG. 8 the position of markers, plotted in a diagram against the position of the pulmonary diaphragm (lung filling)

Both the position of the target volume, as well as the lung filling value matching this position of the target volume, may be read from the planning data sets. An interpolation line may accordingly be plotted from these pairs of values, describing the connection between these two quantities. FIG. 8, showing the position of the markers on the thorax plotted against the lung filling, also includes this second interpolation line.

Figure 7:
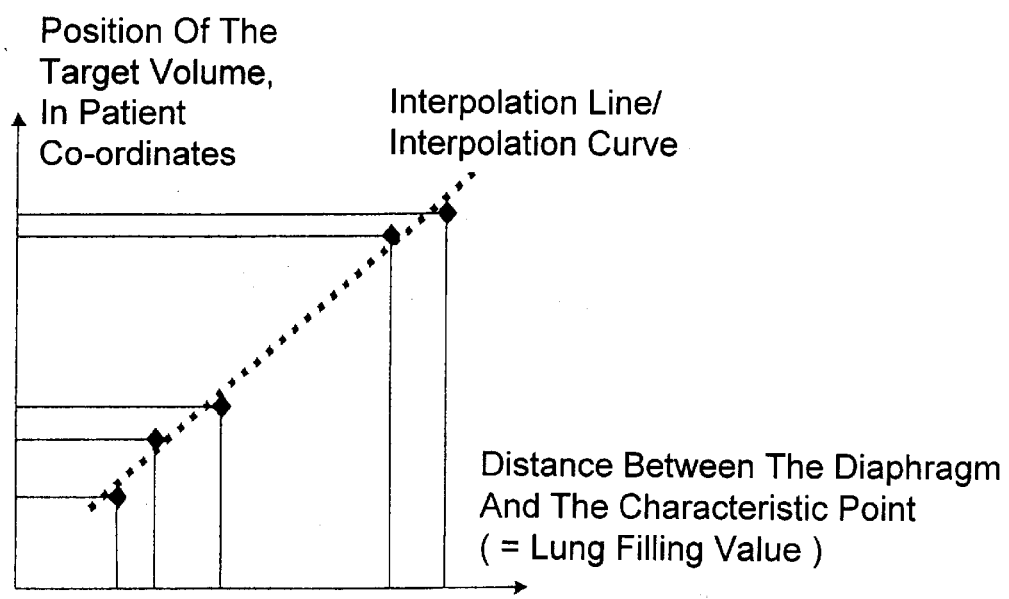
FIG. 7 the position of the radiation target (target volume), plotted in a diagram against the position of the pulmonary diaphragm (lung filling)
Figure 9:
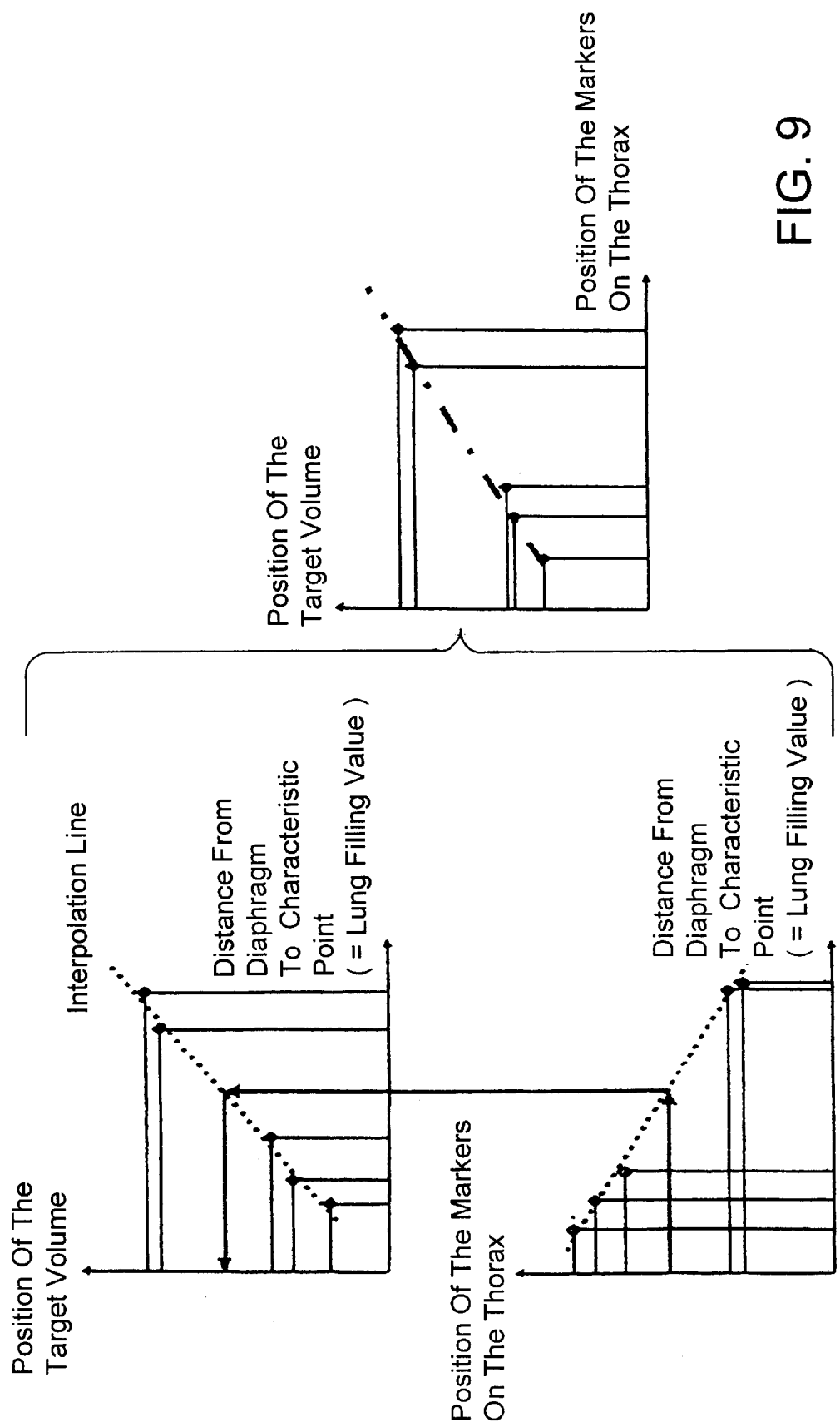
FIG. 9 the diagrammatic deduction of the position of the radiation target (target volume) from the position of the markers.

These two interpolation functions may be mathematically combined in such a way that they may be used to deduce the position of the target volume from the position of the reflecting markers. FIG. 9 shows graphically how the position of the target volume is deduced from the position of the markers. Here, the two diagrams from FIGS. 7 and 8 are placed on the left-hand side, one above the other. The bold line indicates the procedure. In the lower diagram, the lung filling value is then determined from the position of the markers. Given this information, reference to the upper diagram provides the position of the target volume from the lung filling value determined.

This, however, means that when the position of the markers is tracked in real time, the position of the target volume can also be calculated in real time. With the position of the target volume known in real time, breath-controlled irradiation of the patient can be carried out with very high precision.

Compared to detecting the position of the stuck-on markers directly, the method in accordance with the invention has a great advantage which lies in its precision and reliability. This is because the positional reliability of the markers is not sufficiently optimal, due to them slipping on the layers of fat when the patient is moved from capturing the planning data sets to actual radiation exposure. This, however, will always be the case if he has to be taken from the CT to the radiotherapy room.

Markers can only be reliably referenced as long as the patient is lying still. As soon as he stands up, or the markers are removed, association becomes imprecise. Associating the position of the tumour and the position of the markers directly is therefore not optimal. Associating the tumour and the diaphragm in the CT in accordance with the invention, and associating the position of the diaphragm and the markers, still "warm", on the linear accelerator, wherein the method for determining lung filling is employed in accordance with the present invention, solves these problems.

In the foregoing description a preferred embodiment of the invention has been presented for the purpose of illustration and description. It is not intended to be exhaustive or to limit the invention to the precise form disclosed. Obvious modifications or variations are possible in light of the above teachings. The embodiment was chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

What is claimed is:

1. A method for determining the filling of a lung using image data to detect the movement of an anatomical structure that moves with the patient's breathing cycle, the method comprising the steps of, producing an image of a patient's body, determining the position of a first anatomical structure of the patient's body that moves with the patient's breathing cycle with respect to the position of a second anatomical structure of the patient's body that is not spacially affected by the patient's breathing cycle, determining the distance between the first and second anatomical structures, and assigning to this distance a lung filling value.

2. The method as set forth in claim 1, wherein at least two images are produced by transillumination and at least two respective lung filling values are assigned and at least one additional lung filling value is determined by interpolation.

3. The method as set forth in claim 1, wherein at least two images are produced from tomographic imaging methods and at least two respective lung filling values are assigned and at least one additional lung filling value is determined by interpolation.

4. The method as set forth in claim 3, wherein digitally reconstructed x-ray images, obtained from a data set of a tomographic imaging method, are used as the images.

5. The method as set forth in claim 1, wherein the anatomical structure which moves with breathing is a structure which is identifiable on an x-ray image.

6. The method as set forth in claim 1, wherein the anatomical structure which is not spatially affected by breathing is a vertebral body or a part of a vertebral body.

7. The method as set forth in claim 1, wherein at least two images are produced by transillumination and at least two respective transillumination lung filling values are assigned and at least two images are produced from tomographic imaging methods and at least two respective tomographic lung filling values are assigned and the transillumination and the tomographic lung filling values are compared and/or aligned.

8. A method for assisting in radiotherapy during movement of a radiation target due to a patient's breathing cycle, said method comprising the steps of:

acquiring at least two planning images of the patient's body during different times in the patient's breathing cycle, using the planning image data to determine the position of a first anatomical structure of the patient's body that moves with the patient's breathing cycle with respect to the position of a second anatomical structure of the patient's body that is not spacially affected by the patient's breathing cycle, determining the distance between the first and second anatomical structures and assigning to this distance a particular lung filling value, determining a relationship between the position of the radiation target and the lung filling value, acquiring at least two transillumination images of the patient's body during different times in the patient's breathing cycle wherein patient markings are detectable, determining a relationship between the position of the patient markings and the lung filling value, and determining the position of the radiation target using the relationships and the position of the markings.

9. The method as set forth in claim 8, wherein radiotherapy is performed using the determined position of the radiation target.

10. The method as set forth in claim 9, wherein position of the radiation target is used to carry out dynamic repositioning of the patient during radiation exposure.

11. The method as set forth in claim 10, wherein the dynamic repositioning of the patient is a continuous, reverse movement of the patient on a patient's table.

12. The method as set forth in claim 8, wherein the step of acquiring at least two planning images includes digitally reconstructing x-ray images from a tomographic imaging data set where the reconstructed images correspond in angular position and recording distance to the at least two transillumination images.

13. The method as set forth in claim 8, wherein the position of the radiation target is determined in real time or deferred.

14. The method as set forth in claim 8, wherein the position of the patient markings is obtained from:

markings which may be positionally detected and tracked in space by means of a computer-assisted tracking system;

monitoring the contours of the patient using video cameras;

wire strain gauges;

spirometry;

electromyography; or mechanically scanning one or more points on the surface of the patient.

15. The method as set forth in claim 8, wherein the position of the radiation target is used to control application of a radiotherapy beam.

16. The method as set forth in claim 15, wherein the radiotherapy beam is switched on when the radiation target is within a selected tolerance about an axis of the radiotherapy beam or an isocenter of a radiotherapy device.

17. The method as set forth in claim 8, wherein the position of the radiation target is used to position the patient relative to a radiotherapy device such that the radiation target is positioned for optimal radiation exposure time.

18. The method as set forth in claim 8, wherein artificially forced breathing is used to induce a state in the patient in which the lung filling value corresponds to a selected value.

\* \* \* \* \*